United States Patent [19]

Dougherty et al.

[11] 4,001,289
[45] Jan. 4, 1977

[54] ALCOHOL-RHODIUM SEPARATION PROCESS

[75] Inventors: Steven J. Dougherty, St. Albans; Rex C. Wells, Charleston, both of W. Va.

[73] Assignee: Union Carbide Corporation, New York, N.Y.

[22] Filed: Sept. 17, 1974

[21] Appl. No.: 506,864

[52] U.S. Cl. .......................... 260/450; 260/449 L
[51] Int. Cl.² .................. C07C 27/06; C07C 27/26
[58] Field of Search ............... 260/450, 449 R, 637, 260/449 L

[56] References Cited

UNITED STATES PATENTS

| | | | |
|---|---|---|---|
| 2,446,231 | 8/1948 | Johnson | 260/450 |
| 2,922,808 | 1/1960 | Rylander | 260/450 |
| 2,930,810 | 3/1960 | Rylander | 260/450 |
| 2,954,392 | 9/1960 | Rylander | 260/450 |
| 2,979,520 | 4/1961 | Kenton | 260/450 |
| 3,816,549 | 6/1974 | Prinz | 260/637 R |
| 3,833,634 | 9/1974 | Pruett et al. | 260/449 R |

*Primary Examiner*—Howard T. Mars
*Attorney, Agent, or Firm*—George A. Skoler

[57] ABSTRACT

There is described an improvement in the process of recovering alcohol products formed by the homogeneous liquid phase reaction between oxides of carbon and hydrogen in the presence of a rhodium carbonyl complex catalyst which process involves mixing water and an essentially water-immiscible solvent with the solution containing products of such reaction to cause the alcohol products to enter the water phase and the rhodium to enter into the water-immiscible solvent phase. The alcohol products are recovered from the water phase.

4 Claims, No Drawings

ALCOHOL-RHODIUM SEPARATION PROCESS

This invention is concerned with the recovery of alcohol products from a homogeneous liquid phase mixture containing a rhodium complex. More particularly, this invention relates to the separation of the alcohol products of the reaction between oxides of carbon and hydrogen in a homogeneous liquid phase reaction containing a rhodium carbonyl complex.

There are described in copending applications Ser. No. 219,130, filed Jan. 19, 1972 now U.S. Pat. No. 3,833,634, and Ser. No. 462,109, filed Apr. 18, 1974 now U.S. Pat. No. 3,957,857, processes involving the high pressure reaction of oxides of carbon and hydrogen in the presence of a rhodium carbonyl complex catalyst to produce, as most preferred products, polyhydric alcohols such as ethylene glycol, 1,2-propylene glycol and glycerine. It has been pointed out in Ser. No. 462,109 that a preferred rhodium carbonyl complex catalyst is a rhodium carbonyl cluster. The nature of that catalyst under the conditions of the reaction or as it is provided to the reaction can be characterized by its infrared spectrum. However, such catalysts frequently take another structure at temperatures and pressures lower than those used in the reaction.

In a preferred embodiment of those processes, the reaction is conducted in a homogeneous liquid phase mixture, so that the catalyst and even the alcohol products formed from the reaction are in solution. The solution typically requires the presence of a production solvent mainly to keep the catalyst in solution before and after the reaction. The main, and most valuable, products of those processes are high boiling alkane polyols such as ethylene glycol, glycerine and 1,2-propylene glycol, and the secondary, and less valuable products are lower boiling alkanols such as methanol, ethanol, etc. These products were generally removed by distillation, but in a continuous process rather severe changes would be required from the conditions employed in the high pressure reaction to the conditions employed on separation of product.

However, rhodium carbonyl complexes vary in structure based upon the temperature, solvent, ligand, counter-ion, and carbon monoxide and hydrogen pressure imposed upon them. Therefore, a catalyst complex which may be extremely stable in a solution at one temperature such as during the reaction, could precipitate out of the solution at another temperature such as used during product recovery by distillation.

In the case of large scale processes, significant catalyst losses are unacceptable. In the case of the processes of the copending applications, catalyst losses in the order of, for example, about 0.1% by weight of the rhodium content on a per pass basis would probably make the process uneconomical. This can be better appreciated when one realizes that the current dealer price for rhodium metal is about 715 U.S. dollars per troy ounce. In the commercial practice of these processes it will be necessary to avoid a loss of an amount of rhodium metal which causes the cost of product(s) produced to be greater than cost of the same product(s) produced by other competitive processes.

There is described herein an improved extraction process for the recovery of the alcohol products produced by these rhodium catalyzed reactions which reduces catalyst instability during the recovery phase of a continuous process. By the terms "instability" and "unstable", when referring to the catalyst, it is meant that it is reduced to a condition where it becomes, or is, insoluble in the solution from which the product is being recovered.

The process of this invention involved the separation of alcohol products from a liquid phase homogeneous mixture (i.e., the "production solution") obtained from the reaction of oxides of carbon and hydrogen in a solvent solution containing a rhodium carbonyl complex catalyst in a manner which minimizes catalyst instability. This is accomplished by mixing the mixture with water and an essentially water immiscible organic extraction solvent for the rhodium complex present in the mixture, forming a water phase containing the alcohol product and an organic solvent phase containing essentially all of the rhodium complex, and separating the phases to effect recovery of product from the water phase without effecting significant catalyst losses since the water phase is essentially free of the rhodium.

The typical production solution (i.e., "liquid phase homogeneous mixture") which is to be treated in accordance with this invention will contain the "product(s)" of the reaction, such as the alcohols: ethylene glycol, glycerine, propylene glycol, methanol, ethanol, propanol; esters: ethylene glycol monoformate, methyl formate, ethyl formate; and the like; the catalyst in the form of a rhodium complex and a production solvent for the catalyst which is also compatible with the products of the reaction. The amount of product in the solution can vary greatly, from about 1 to about 75 weight per cent of the solution. The production solvent can be present in a broad range, such as from about 25 to about 99 weight per cent of the solution. The catalyst concentration can vary greatly, from about $1 \times 10^{-6}$ weight per cent, or even less, to about 30 weight per cent, or more, based on its rhodium metal content. The composition of the liquid homogeneous mixture being treated according to this invention is not narrowly critical. All that is required in the solution (or mixture) is any amount of reaction product which is to be recovered, and any amount of a rhodium complex solvated by a production solvent.

The rhodium complex present in the production solution does not have to have the structure of the rhodium carbonyl complex which catalyzed the reaction between the CO and $H_2$. In those cases where the rhodium carbonyl complex acting as the catalyst has the structure

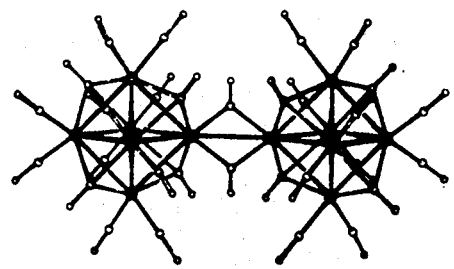

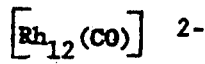

the rhodium carbonyl complex which exists in the homogeneous mixture may be an anion of the structure

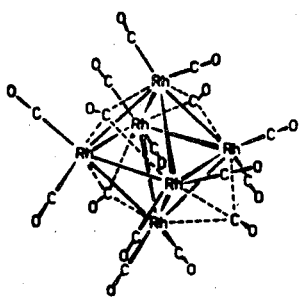

$Rh_6(CO)_{16}$ or it may be the anion of lower rhodium containing compounds, from monorhodium carbonyl and up. All that is required for the process of this invention is that the rhodium values, as a complex, employed in the reaction, be in solution.

The solubilization of the rhodium carbonyl complex is typically dependent upon the production solvent used to effect the homogeneous mixture. The desired solvent is any liquid material which dissolves or keeps in solution the components of the homogeneous mixture taken from the reactor. It must be solution compatible with the reaction products and the rhodium carbonyl complex.

Illustrative production solvents which are generally suitable in making the homogeneous mixture, include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxyethyleneoxypropylene glycol, etc.; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, methyl butyrate, methyl propionate, ethyl butyrate, methyl laurate, etc.; water; anhydrides such as phthalic anhydride, acetic anhydride, etc.; gamma-butyrolactone, delta-valerolactone, and others. Tetrahydrofuran, dioxane, and the mono and dialkylethers of triethylene and tetraethylene glycol and gamma-butyrolactone are generally preferred solvents.

Counter-ions, such as ligands and cations, may be associated with the rhodium carbonyl complex in the homogeneous mixture. They are used to enhance the catalyst's functionality in the course of reaction. The kinds of each which may be selected is dependent upon the conditions used to effect the reaction between CO and hydrogen. Very high pressure reactions require only soluble rhodium, oxide of carbon (such as carbon monoxide) and hydrogen to form a desirable rhodium carbonyl complex.

The counter-ions may be rhodium per se, hydrogen, ammonia any monovalent or polyvalent metal, and a broad range of organic compounds, such as those characterized hereinafter as ligands.

The monovalent or polyvalent metal counter-ions may include lithium, sodium, potassium, rubidium, cesium francium, beryllium, magnesium, calcium, strontium, barium, radium, scandium, yttrium, the rare earth metals (especially, e.g., cerium, praseodymium, and europium), titanium, zirconium, hafnium, manganese, rhenium, iron, ruthenium, osmium, cobalt, rhodium, iridium, nickel, palladium, platinum, copper, silver, gold, boron, aluminium, gallium, indium, and thallium.

The organic counter-ions may result from "complexing" organic compounds with the rhodium carbonyl complex ions or by ionically associating with them.

These organic counter-ion complexes are formed from complexing the rhodium carbonyl complex with a coordination compound which is formed by the union of one or more electronically rich molecules or atoms capable of independent existence with one or more electronically poor molecules or atoms, each of which is also capable of independent existence. These complexes are derived from the association of organic ligands with solutions of rhodium containing carbonyl complexed therewith.

Organic ligands which are suitable in the practice of the invention contain at least one nitrogen atom (hereinafter called Lewis base nitrogen atom) and/or at least one oxygen atom (hereafter called Lewis base oxygen atom), said atoms possessing a pair of electrons available for the formation of coordinate bonds with rhodium. Desirably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with rhodium. In suitable embodiments, the organic ligands contain from 2 and upwards to 4 Lewis base atoms, preferably from 2 to 3 such atoms, and most preferably 2 Lewis base atoms. These organic ligands are said to be multidentate or polydentate, that is to say, such ligands are bidentate, tridentate, or quadridentate, depending on whether 2, 3, or 4 Lewis base atoms are involved in the formations of complexed structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino ($-N=$), amino

nitrilo (N ≡ ), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the

group and the "oxy" oxygen in the

group that are the Lewis base atoms. The organic ligands may also contain other atoms and/or groups such as alkyl, cycloalkyl, aryl, chloro, thiaalkyl, trialkylsilyl, and the like.

Illustrative organic nitrogen ligands include for instance, N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine, 2,2'-dipyridyl, methyl-substituted 2,2'-dipyridyl, ethyl-substituted 2,2'-dipyridyl, 1,4-diaxabicyclo [2.2.2] octane, methyl-substituted 1,4-diazabicyclo [2.2.2] octane, purine, 2-aminopyridine, 2-(dimethylamino) pyridine, 1,10-phenanthroline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, and the like.

Illustrative organic oxygen ligands include, by way of illustrations, glycolic acid, methoxyacetic acid, ethoxyacetic acid, diglycolic acid, thiodiglycolic acid, diether ether, tetrahydrofuran, dioxane, tetrahydropyran, pyrocatechol, citric acid, 2-methoxyethanol, 2-ethoxyethanol, 2-n-propoxyethanol, 2-n-butoxyethane, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl) iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other organic counter-ions are formed by ionic association with, e.g., the rhodium carbonyl cluster ions. They are from organic compounds which possess Lewis base nitrogen atoms and typically are composed of carbon, hydrogen and nitrogen. Illustrative of such compounds are, e.g., piperidine, 2-methylpiperidine, 3-methylpiperidine, pyridine, 2-methylpyridine, 4-ethylpiperidine, triethylamine, benzyltrimethylammonium acetate and formate, tri-n-butylamine, dibutylamine, methylamine, dodecylamine, morpholine, aniline, benzylamine, octadecylamine, naphthylamine, cyclohexylamine, and the like.

The extraction solvent may be any organic compound which has the following characteristics and relationships:

1. It is liquid under the conditions of extraction.
2. It is essentially immiscible in water, i.e., it is not more than about 10 weight per cent soluble in water and water is not more than about 10 weight per cent soluble in the extraction solvent. The significant aspect of this limitation is the effect compatibility of the extraction solvent with water has on the preferential extractability of the solvent for the rhodium values in the production solution. The solubility of the extraction solvent in water should not be such as to adversely affect the distribution of the rhodium values so that the undesirable amounts of rhodium are distributed in the predominently water phase.
3. The production solvent is preferably more readily soluble in the extraction solvent than it is in water. For example, when blended with an equal volume of water and extraction solvent, determined at 25° C., and then left to stand, two liquid phases are formed, a water phase and an extraction solvent phase, and more of the production solvent is in the extraction solvent phase. This relationship is not critical, and one may characterize it by saying that the activity coefficient of the production solvent in the extraction solvent is less than the activity coefficient of the production solvent in the water phase.
4. It is essentially non-reactive with water and the alcohol products.
5. It contains a characteristically electron deficient atom or group which withdraws electrons from a hydrogen atom therein to cause an electron deficiency on the hydrogen atom.

In the final analysis, when the production solution is mixed with both the extraction solvent and water, each can be added to the production solution in any order, two immiscible phases must form. The water phase should carry the alcohol products and the extraction solvent phase should contain the rhodium values. The production solvent may be in either phase but will typically be in the extraction solvent phase.

The extraction solvent may be further characterized by the following test:

When the extraction solvent is intermixed at 25° C with an equal volume amount of water and the intermixture is thoroughly blended at 25° C. in a vessel of sufficient size with an equal volume of the production solution [taken from the reaction of an equal molar quantity of hydrogen and carbon monoxide fed to an autoclave at 1000 atmospheres containing 3,000 parts per million, on weight basis, of rhodium dissloved in a production solvent at 250° C. for a period of time sufficient to form a product solution containing at least 6 per cent by weight of ethylene glycol,] there is formed in the vessel, on standing, two layers, one which principally contains water and the ethylene glycol and the other layer principally contains the extraction solvent and the rhodium metal content (at least 95 weight per cent thereof) which was in the production solution.

In the above the importance of this invention is finding that by the use of a combination of water and the extraction solvent one can separate the alcohol products from the predominent amount of the rhodium contained in the production solution without converting undesirable amounts of the rhodium content into insoluble materials which are lost in the equipment train. Water, alone, will not extract the alcohol products from the production solution and the rhodium content. The extraction solvent, alone, will not separate the alcohol products from the rhodium content. It is only from a combination of the two that the alcohol products can be removed from their association with the predominent rhodium content of the production solution.

It is not critical to this invention that the production solvent remain in the extraction solvent phase. It can be carried into the water phase and by distillation, be separated from the alcohol products and water; however, the production solvent should not be carried into the water phase if it carries with it an undesirably large portion of the rhodium content.

Selection of the extraction solvent is predicated on two interrelated, criteria, which are: (1) its relative water insolubility and (2) its preference for solubilizing the rhodium content in the production solution. Once the alcohol products are separated from the rhodium content, they are easily recovered by distillation without causing losses of rhodium.

Illustrative of specific extraction solvents which conform to the preceding criteria are, by way of example only, the following:

$CH_2Cl_2$
$CH_3Cl$
$CHCl_3$
$Cl_2CHCHCl_2$
$Cl_2CHCH_2CHCl_2$
$Cl_3CCHClCCl_3$
$Cl_2CHCHClCHCl_2$
$CF_3CHClCF_3$
$CF_3CH_2CH_3$
$ClCH_2CH_2CH_2Si(CH_3)_3$
$ClCH_2CH_2Si(CH_3)_3$
$CH_3CH_2CN$
$CH_3CH_2CH_2CN$
$ClCH_2CH_2CH$
$NCCH_2CH_2Si(CH_3)_3$
$NCCH_2CH_2CH_2Si(CH_3)_3$
$CH_3CH_2CH_2CHO$
$CH_3NO_3$
$CH_3CH_2NO_3$
$[NCCH_2CH_2SiCH_3O]_4$
$[ClCH_2CH_2CH_3SiCH_3O]_3$

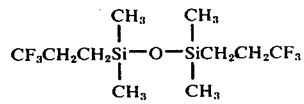

$ClCH_2CH_2CH_2Si(C_6H_5)_3$

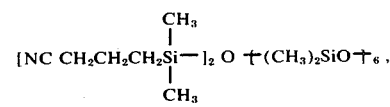

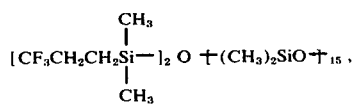

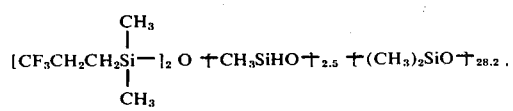

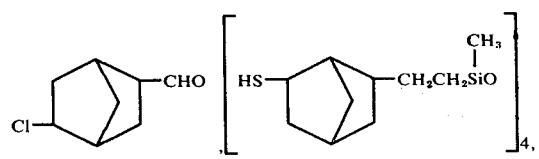

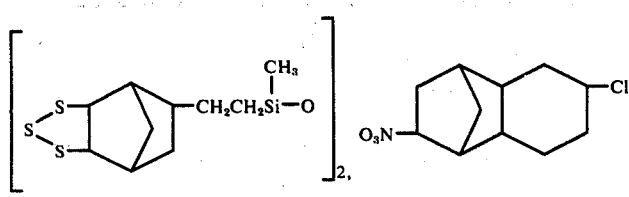

The extraction procedure is not critical to the invention. Neither is the amount of extraction solvent and water. Any method which effects contact between the production solution and an amount of extraction solvent and water sufficient to remove a desired amount of alcohol product from the production solvent and retain the rhodium values in the extraction solvent phase is adequate for this invention. The ratio of water to extraction solvent may range, on a volume basis, from about 0.01 to 100, though it is preferred to use a ratio of 0.1 to 10. In the preferred embodiment, the amount of water and extraction solvent is desirably sufficient to essentially remove the alcohol products, specifically ethylene glycol, to the water phase and retain the rhodium values in a production solvent-extraction solvent phase.

Either the water or the extraction solvent may be first admixed with the production solution followed by the other. Alternatively, water and the extraction solvent may be premixed and blended with the production solution. Another procedure involves the simultaneous addition of the production solution, extraction solvent and water to a vessel with agitation.

The extraction process may be effected at ambient temperatures and pressures, though temperatures ranging from about 0° to about 200° C., preferably from about 15° to about 125° C., may be employed effectively. Pressures ranging from subatmospheric to superatmospheric pressures are suitably employed, e.g., 0.1 mm. Hg pressure to about 500 atmospheres pressures are contemplated as employable.

Any of the known extraction procedures may be employed, such as mixing in a vessel with stirring followed by settling and decantation, or countercurrent extraction in which water and the extraction solvent are countercurrently fed either one premixed with the production solution, or by single direction extraction in a stirred column, and the like.

The removed alcohol products may be isolated from the water by fractional distillation and the rhodium values can be recovered by distillation of the extraction solvent or by chemical conversion of the rhodium to an isolatable water soluble species which can thereafter be converted in a known manner for re-use in making reaction product.

The following illustrates this invention:

The following table describes data on the composition of the production solution treated, the amount of water, production solution and extraction solvent added, and the amount of rhodium and ethylene glycol separated in the extraction solvent and water phases. In each of the examples in the table, the extraction solvent and production solution were mixed in an appropriately sized separatory funnel to which was added water. The contents of the funnel were shaken thoroughly by hand. Then the funnel was allowed to rest until the two liquid phases were completely separated into separate layers. Such took from a few minutes to about 24 hours in the various examples. The separate layers were separated and analyzed to provide the data recited in the table.

TABLE

DESCRIPTION OF PRODUCTION SOLUTION

| | | | | Component Concentration | | | | |
|---|---|---|---|---|---|---|---|---|
| Example No. | Reaction Temperature (° C.) | Reaction Pressure (psig) | Reaction Solvent[a] | Reaction Solvent (Weight %) | Ethylene Glycol (Weight %) | Methanol (Weight %) | Rhodium (ppm)* | Other Counter-ion (ppm)[b*] |
| 1 | 220 | 10,000 | TG | 94.3 | 3.5 | 1.2 | 2430 | Cs(526) |
| 2 | 220 | 10,000 | TG | 94.3 | 3.5 | 1.2 | 2430 | Cs(526) |
| 3 | 220 | 10,000 | TG | 94.3 | 3.5 | 1.2 | 2430 | Cs(526) |
| 4 | 220 | 10,000 | TG | 94.3 | 3.5 | 1.2 | 2430 | Cs(526) |
| 5 | 220 | 8,000 | TG | 86.2 | 7.5 | 3.4 | 5050 | $P_2N$ (7350) |
| 6 | 220 | 8,000 | TG | 86.2 | 7.5 | 3.4 | 5050 | $P_2N$ (7350) |
| 7 | 220 | 8,000 | TG | 86.2 | 7.5 | 3.4 | 5050 | $P_2N$ (7350) |
| 8 | 230 | 8,000 | TG | 92.8 | 6.3 | 0.3 | 810 | Cs(176) |
| 9 | 220 | 10,000 | TG | 94.3 | 3.5 | 1.2 | 2430 | Cs(526) |
| 10 | 220 | 8,000 | TG | 86.2 | 7.5 | 3.4 | | $P_2N$ |
| 11 | 220 | 10,000 | TG | 94.3 | 3.5 | 1.2 | 2430 | Cs(526) |
| 12 | 220 | 10,000 | TG | 94.3 | 3.5 | 1.2 | 2430 | Cs(526) |
| 13 | 220 | 10,000 | TG | 94.3 | 3.5 | 1.2 | 2430 | Cs(526) |
| 14 | 220 | 10,000 | TG | 94.3 | 3.5 | 1.2 | 2430 | Cs(526) |
| 15 | 240 | 8,000 | BL | 88.3 | 4.3 | 5.5 | 8000 | Cs(1800) |

COMPOSITION OF SEPARATED LAYERS

| | | | | Extraction Solvent Layer | | Aqueous Solution Layer | | |
|---|---|---|---|---|---|---|---|---|
| Example No. | Extraction Solvent | Aqueous Solution | Volumetric Ratios of Process Streams (Production Solution: Aqueous Solution: Extraction Solvent) | Rhodium (ppm)[c*] | Ethylene Glycol (Weight % O) | Rhodium (ppm)* | Ethylene Glycol (Weight %) | Rhodium Retained[d](%) |
| 1 | Methylene Chloride | Water | 1:1:2 | 800 | Trace | 14.4 | All | 99.4 |

TABLE-continued

| | | | | | | | | |
|---|---|---|---|---|---|---|---|---|
| 2 | Chloroform | Water | 1:1:1 | 1200 | Trace. | 7.2 | All | 99.7 |
| 3 | 1,1,2,2-Tetrachloroethylene | Water | 2:1:4 | 800 | — | 121 | — | 97.5 |
| 4 | 1,2-Dichloro-Ethylene | Water | 2:1:4 | 800 | — | 140 | — | 97.1 |
| 5 | Butyraldehyde | Water | 1:1:2 | 1700 | 2.1 | 8.8 | 4.0 | 99.8 |
| 6 | Nitromethane | Water | 1:1:2 | 1700 | 0.4 | 170 | 5.8 | 96.6 |
| 7 | Proprionitrile | Water | 1:1:2 | 1700 | 1.1 | 342 | 5.3 | 93.2 |
| 8 | Heptane | Water | 3:1:5 | 0ᶠ | — | all | — | — |
| 9 | Carbontetrachloride | Water | 1:1:2 | g | — | all | — | — |
| 10 | Triethylamine | Water | 1:1:2 | g | — | all | — | — |
| 11 | Methylene Chloride | Water with 400 ppm Cesium* | 2:1:4 | 800 | — | 121 | — | 97.5 |
| 12 | Methylene Chloride | Water with 1000 ppm Cesium* | 2:1:4 | 800 | — | 101 | — | 97.9 |
| 13 | Methylene Chloride | Water with 2500 ppm Cesium* | 2:1:4 | 800 | — | 95 | — | 98.1 |
| 14 | Methylene Chloride | Water with 5000 ppm Cesium* | 2:1:4 | 800 | — | 96 | — | 98.1 |
| 15 | Methylene Chloride | Water | 1:1:2 | 2700 | Trace | 27.7 | All | 99.7 |

ᵃTG means dimethyl ether of tetraethylene glycol (tetraglyme); BL means γ-butyrolacetone.
ᵇCs means cesium (added as Cesium 2-hydroxypyridinate); P₂N means bistriphenylphosphine iminium acetate.
ᶜCalculated from the amount of Rhodium in the Production Solution after dilution by the Extraction Solvent.
ᵈRetained Rhodium = $\frac{(A \times B) - (C \times D)}{A \times B}$, where A is weight of Rhodium in Production Solution
B is volume of Production Solution
C is weight of Rhodium in aqueous phase
D is volume of aqueous phase ᶠTaken as 0 because Extraction Solvent layer is clear.
ᵍRhodium in Extraction Solvent is estimated as less than 10 weight % of initial amount of rhodium taken on basis of solution colors.
*ppm means part per million by weight

What is claimed is:

1. In the extraction process of separating the alcohol products, including ethylene glycol, of the high pressure production solvent containing, homogeneous liquid phase reaction between oxides of carbon and hydrogen in the presence of a rhodium carbonyl complex catalyst, whereby the alcohol products of the reaction and rhodium from said catalyst are in solution in said production solvent, the improvement which comprises mixing said solution with water and an organic extraction solvent in which said production solvent is more soluble than it is in water, which extraction solvent is characterized as being liquid under the conditions of the extraction, it is essentially immiscible in water, it is essentially non-reactive with water and the alcohol products, the extraction solvent being further characterized in the formation of two layers (one principably containing water and the ethylene glycol and the other principally containing the extraction solvent and the rhodium content which was in the production solution) when it is intermixed at 25° C with an equal volume of water and blended at 25° C with an equal volume of production solution, whereby said products are separated into an aqueous phase and the catalyst is separated into the extraction solvent phase.

2. The process of claim 1 wherein the production solvent comprises the dimethyl ether of tetraethylene glycol.

3. The process of claim 2 wherein the extraction solvent is methylene chloride.

4. The process of claim 2 wherein the extraction solvent is chloroform.

* * * * *